US007497990B2

(12) United States Patent
Blenke et al.

(10) Patent No.: US 7,497,990 B2
(45) Date of Patent: Mar. 3, 2009

(54) PROCESS FOR THE DESTRUCTION OF MICROORGANISMS ON A PRODUCT

(75) Inventors: Timothy James Blenke, Neenah, WI (US); Tom Ehlert, Neenah, WI (US); James Jay Tanner, Winneconne, WI (US); David W. Koenig, Menasha, WI (US); Bernard Cohen, Duluth, GA (US)

(73) Assignee: Kimberly-Clark Worldwide Inc., Neenah, WI (US)

( * ) Notice: Subject to any disclaimer, the term of this patent is extended or adjusted under 35 U.S.C. 154(b) by 752 days.

(21) Appl. No.: 11/026,235

(22) Filed: Dec. 30, 2004

(65) Prior Publication Data

US 2009/0035178 A1 Feb. 5, 2009

(51) Int. Cl.
*A61L 2/00* (2006.01)
*C12Q 1/68* (2006.01)
*F28D 21/00* (2006.01)
*C09C 1/00* (2006.01)
*B29C 65/00* (2006.01)

(52) U.S. Cl. .............................. 422/22; 422/2; 422/204; 422/157.42; 422/157.15; 435/6; 156/73.2

(58) Field of Classification Search .................. 422/20, 422/204, 157.42, 157.15; 156/73.2
See application file for complete search history.

(56) References Cited

U.S. PATENT DOCUMENTS

| 5,449,502 | A | * | 9/1995 | Igusa et al. .................. 422/292 |
| 5,707,470 | A | | 1/1998 | Rajala et al. |
| 6,090,346 | A | | 7/2000 | Rose et al. |
| 6,171,548 | B1 | | 1/2001 | Rose et al. |
| 6,241,162 | B1 | * | 6/2001 | Takahashi et al. ......... 239/102.2 |
| 6,264,543 | B1 | | 7/2001 | Garcia et al. |
| 6,311,573 | B1 | | 11/2001 | Bhardwaj |
| 6,576,188 | B1 | | 6/2003 | Rose et al. |
| 2002/0164274 | A1 | * | 11/2002 | Haggett et al. ............... 422/128 |
| 2003/0046897 | A1 | * | 3/2003 | Kitajima et al. ............ 53/133.2 |
| 2004/0022668 | A1 | | 2/2004 | Kitchen |
| 2004/0028552 | A1 | | 2/2004 | Bhardwaj et al. |
| 2004/0186384 | A1 | * | 9/2004 | Babaev ....................... 600/489 |

FOREIGN PATENT DOCUMENTS

| DE | 27 26 750 A1 | 12/1978 |
| EP | 0 083 448 A2 | 7/1983 |
| JP | 03151836 | 6/1991 |
| JP | 03224570 | 10/1991 |
| WO | WO 99/33495 A2 | 7/1999 |

OTHER PUBLICATIONS

Kelli Hoover et al., *Destruction of bacterial spores by phenomenally high efficiency non-contact ultrasonic transducers*, Materials Research Innovations (2002) 6:291-295; published online Oct. 23, 2002.
International Search Report from PCT/US2005/043750, dated May 4, 2006.

* cited by examiner

*Primary Examiner*—Walter D Griffin
*Assistant Examiner*—Lydia Edwards
(74) *Attorney, Agent, or Firm*—Armstrong Teasdale LLP

(57) ABSTRACT

A process for the destruction of microorganisms on a product using ultrasonic energy is disclosed. The process comprises contacting a product with an ultrasonic horn assembly and generating ultrasonic energy sufficient to result in a microorganism destruction rate of at least a 1-log kill.

35 Claims, No Drawings

PROCESS FOR THE DESTRUCTION OF MICROORGANISMS ON A PRODUCT

FIELD OF THE INVENTION

The present invention generally relates to a process for substantially minimizing or eliminating microorganisms on or in a product. More specifically, the present invention relates to a process for the substantial destruction of microorganisms on or in a product using ultrasonic energy, wherein the microorganism destruction rate on the product is at least about a 1-log kill.

BACKGROUND OF THE INVENTION

Wherever there is a source of nutrition and moisture, microorganisms will grow. This is often the case even in extreme environmental conditions. These microorganisms may spoil food, interfere with manufacturing processes, decay consumer products, or affect human health. Consumer products require the substantial elimination of these unwanted microorganisms, since these products are frequently the delivery means for bringing the microorganisms into or onto the human body. Consumer products that can carry microorganisms include paper products, foodstuffs, clothing, medical devices, cosmetics, and a multitude of other consumer health and hygiene products.

In addition to the need for reducing the number of microorganisms on consumer products, recent bioterror attacks have prompted the need for the decontamination of products that have been purposefully tainted with microorganisms. Aerosolized anthrax spores (*Bacillus anthracis*) have been inserted in and upon articles of mail, resulting in infection and death. Thus, there is a need to protect postal employees and potential recipients of microorganism-tainted letters and packages sent through the mail.

Control of microbial growth can be achieved by inhibition of growth, killing, or removing the microorganisms from the environment. Pasteurization and sterilization are common means to control microbial growth. Pasteurization is the process of removing or reducing the level of harmful bacteria from a product. Sterilization is the process of killing or removing all living organisms and viruses from a product. Microorganism death is an exponential function; therefore it is linear when plotted on a log scale. The rate of microbial destruction is termed an "x-log reduction" or "x-log kill," which corresponds to the percentage of microorganisms killed or inactivated. For example, if 99% of all microorganisms in or on a given product have been killed or inactivated, this is equivalent to a 2-log kill. If 99.9% of all microorganisms in or on a given product have been killed or inactivated, this is equivalent to a 3-log kill; and so on. A 6-log kill, wherein 99.9999% of all microorganisms have been killed or inactivated, is the destruction rate at which a product is considered "sterilized."

Several methods exist to assist in the decontamination of microorganisms from products. For example, many manufacturing processes employ biocides in process streams and/or post-process treatment of the finished product. However, process stream biocide treatments can be ineffective and harmful to the environment. Other methods include autoclave sterilization, which involves using steam under pressure. The high heat and pressure of autoclave sterilization destroys many pathogenic bacteria. However, steam heat cannot be used in many applications because the elevated temperatures and wet environment would destroy the aesthetic and functional properties of the product.

Electromagnetic irradiation is another method for removing or reducing the amount of microorganisms in or on products. Microwaves, ultraviolet (UV) radiation, X-rays, and gamma rays from sources such as Cobalt 60 are commonly used to reduce the number of pathogens in or on products. UV irradiation, which does not penetrate solid, opaque, or light absorbing materials, can be useful for decontaminating ambient air, surfaces, and liquids that do not absorb the UV waves. Gamma rays and X-rays are more penetrating, and can be used to decontaminate a wider range of products. However, these decontamination methods are relatively more expensive, difficult to use, and require a substantial amount of shielding between the workers and the radiation source. Another significant disadvantage of gamma irradiation is the relatively long exposure time required to effectively decontaminate the product. This, coupled with the high cost, makes irradiation an impractical method in many high-throughput manufacturing and process streams where rapid decontamination is desired.

Yet another method for inactivation or elimination of microorganisms in or on products is through the use of sonication. Sonication is the use of high power, low frequency ultrasound with a liquid medium as the ultrasonic wave carrier. The liquid medium acts as a physical coupling device that transmits the ultrasonic energy through the medium and onto the product to be decontaminated. Similar to autoclave sterilization, however, immersing the product into a liquid medium may destroy its aesthetic and functional properties.

The use of ultrasonic energy for microbial decontamination without the use of a physical coupling device is also known. For example, in U.S. Pat. No. 6,576,188, Rose et al. describe the simultaneous exposure of an item to ultraviolet light and ultrasonic wave energy in a non-aqueous environment, such as air, to eliminate microbial contamination. By way of further example, U.S. Patent Application 2004/0028552 describes the use of ultrasonic energy for microbial decontamination using a "non-contact" ultrasonic apparatus in ambient air. However, due to the significant attenuation of the ultrasound energy when transmitted through a compressible medium, such as gas or ambient air, in addition to being an ineffective method of applying ultrasound, the process is sensitive to the physical distance between the acoustic source and the treated materials as well as the materials' orientation to the acoustic waves.

These examples, however, do not achieve a significant rate of killing at a rapid enough pace for many manufacturing and process streams. Moreover, destroying microorganisms on products using these processes may harm the aesthetic and functional properties of the product.

Therefore, it would be desirable to provide a process for the destruction of microorganisms on a product in a relatively short period of time and with a relatively high microorganism destruction rate. It would also be desirable to provide a process for the destruction of microorganisms on a product in a relatively short period of time and with a relatively high microorganism destruction rate, without damaging the aesthetic and functional properties of the product.

SUMMARY OF THE INVENTION

Among the various aspects of the present invention is a process for the substantial destruction of microorganisms on a product. The process uses ultrasonic energy to substantially destroy microorganisms on the product without substantially harming the aesthetic and functional properties of the product. The product is contacted with an ultrasonic horn assembly and the horn suitably excited to produce ultrasonic energy to destroy microorganisms. One significant advantage of the process as described herein is the high speed at which products can be pasteurized or sterilized. This is directly related to the fact that the ultrasonic energy exposure time is of very short duration.

Briefly, therefore, the present invention is directed to a process for the destruction of microorganisms on a product using ultrasonic energy. The process comprises contacting the product with an ultrasonic horn assembly comprising an ultrasonic horn and an anvil. A single pulse is generated from the ultrasonic horn assembly which excites the ultrasonic horn to amplitudes that will generate ultrasonic energy at a frequency of an effective amount to destroy the microorganisms on the product. The pulse preferably lasts for not more than about 5 seconds, and the microorganism destruction rate is at least about a 1-log kill. Additionally, the process of the present invention does not harm the aesthetic and functional properties of the product.

The present invention is also directed to a process for the destruction of microorganisms on a product using multiple pulses generated from the ultrasonic horn assembly. In one embodiment, two to five pulses are generated from the ultrasonic horn assembly. In this embodiment, each pulse preferably lasts for not more than about 1 second. In another embodiment, six to ten pulses are generated from the ultrasonic horn assembly. In this embodiment, each pulse preferably lasts for not more than about 0.55 seconds.

Other objects and features will be in part apparent and in part pointed out hereinafter.

DETAILED DESCRIPTION OF THE INVENTION

In accordance with the present invention, a process for the destruction of microorganisms on a product is disclosed that includes the use of ultrasonic energy. The novel process described herein results in a microorganism destruction rate of at least about a 1-log kill, and does not substantially harm the aesthetic and functional properties of the product. Surprisingly, it has been discovered that the ultrasonic energy process described herein can be utilized in high speed machinery without the drawbacks typically associated with ultrasonics.

Generally, the process of the present invention comprises contacting the product to be decontaminated with one or more components of an ultrasonic horn assembly, sometimes referred to as an acoustic source. An ultrasonic horn assembly typically includes a power supply, an ultrasonic transducer, one or more amplifying (or attenuating) waveguides commonly referred to as boosters, a terminating waveguide commonly referred to as an ultrasonic horn, an actuator, and an anvil. The high frequency vibration created by the ultrasonic horn assembly is typically created through the application of the ultrasonic transducer and the power supply. The power supply supplies an alternating voltage at an ultrasonic frequency to the ultrasonic transducer. The ultrasonic transducer generates a continuous mechanical vibration referred to as a longitudinal compression wave. The booster(s) then increases the amplitude of the compression wave. This longitudinal compression wave is transmitted from the ultrasonic transducer through one or more waveguides, which are designed to efficiently transmit a vibration of a given frequency. The ultrasonic horn may also function to amplify the vibration wave that is transmitted from the ultrasonic transducer to achieve a more desirable level of ultrasonic energy.

Typically, the vibration is then coupled into the ultrasonic horn. The ultrasonic horn is designed to be the working tool of the ultrasonic horn assembly and is where the ultrasonic energy is applied to the product through an energy transfer surface. Because the ultrasonic horn is also a waveguide, it is designed to efficiently transmit a vibration of a given frequency and may, in some circumstances, further amplify the vibration wave.

The ultrasonic transducer, the booster, and the ultrasonic horn are typically mounted into an actuator, which functions to: (1) hold the components in a manner that does not constrain their vibration; (2) actuate the ultrasonic horn assembly to bring the ultrasonic horn into working contact with the anvil; and (3) apply a static force. The anvil is designed to be a rigid surface for the ultrasonic horn to work against.

For purposes of the present invention, the ultrasonic horn assembly may comprise an ultrasonic horn and an anvil. The ultrasonic horn assembly also inherently includes a power source, an ultrasonic transducer, and one or more boosters to ultrasonically excite the ultrasonic horn; however, any mechanism which provides the desired excitation can be used in the present invention. Such mechanisms are known to those skilled in the art. An excitation mechanism, therefore, ultrasonically excites the ultrasonic horn to thereby deliver the ultrasonic energy through the energy transfer surface on the ultrasonic horn.

In one embodiment of the present invention, the ultrasonic horn is a rotary ultrasonic horn. The ultrasonic horn may be constructed of any metal having suitable acoustical and mechanical properties. Suitable metals include aluminum, monel, titanium, and some alloy steels. In a preferred embodiment, the metal can be a titanium-based material, such as commercially pure titanium, or titanium alloy.

Variables such as the diameter, mass, width, thickness, and overall configuration of the ultrasonic horn are not narrowly critical. However, the variables do determine the particular frequency and amplitude at which the ultrasonic horn resonates and vibrates. In particular, the physical variables of the ultrasonic horn, such as diameter, mass, width, thickness, and overall configuration may be selected such that the device resonates in a desired mode, i.e., a fundamental resonant mode under a given set of conditions, at a particular frequency, and with a desired amplitude. For purposes of the present invention, the ultrasonic horn is preferably one that is excited to amplitudes that will generate ultrasonic energy at a frequency of an effective amount to destroy the microorganisms on a product by rupturing their cell walls, by inactivating them, or by otherwise removing them from the product.

The ultrasonic horn assembly of the present invention also includes an anvil with which the horn acts. In one embodiment of the present invention, the anvil is a rotary anvil. The anvil has an outer peripheral surface located parallel to the energy transfer surface of the ultrasonic horn. It is contemplated that there is a space in between the energy transfer surface of the ultrasonic horn and the anvil, such that the product to be decontaminated is placed in or passes through the space and contacts the ultrasonic horn and/or the anvil while ultrasonic energy is being generated by the ultrasonic horn.

According to the process of the present invention, the product to be decontaminated is placed in or directed through the space in between the energy transfer surface of the ultrasonic horn and the outer peripheral surface of the anvil, making contact with one, or both components. As the product contacts the ultrasonic horn and/or the anvil, it is subjected to ultrasonic energy generated by the ultrasonic horn assembly. The ultrasonic horn and anvil may themselves be in contact with each other prior to the insertion of the product therebetween. Alternatively, if the ultrasonic horn and anvil are held at a fixed distance apart, the space in between them needs to be less than the thickness of the product being treated so that a force is applied to the product when the ultrasonic horn is excited.

Upon excitation the ultrasonic horn cyclically expands and contracts at a particular amplitude. This expansion and contraction is the driving force for the ultrasonic energy used to destroy microorganisms on the product. This expansion and contraction corresponds to an ultrasonic energy value applied to the product traveling in the space in between the ultrasonic horn's energy transfer surface and the outer peripheral surface of the anvil. Different products and processes may require different ultrasonic energy values to effectively destroy microorganisms on the product without harming its aesthetic and functional properties. For example, the amplitude may be less than about 0.013 centimeters for many product and process applications. Preferably, the ultrasonic horn expands and contracts at a total amplitude of from about 0.0006 centimeters to about 0.006 centimeters. More preferably, the ultrasonic horn expands and contracts at a total amplitude of from about 0.004 centimeters to about 0.006 centimeters.

The ultrasonic energy applied to the product through the contact with the ultrasonic horn assembly is generated at a frequency which exerts energy in the form of longitudinal plane waves directed perpendicular to the plane of the product as it contacts the ultrasonic horn and the anvil. Preferably, the frequency of the ultrasonic energy is less than 50 kHz. More preferably, the frequency of the ultrasonic energy is from about 20 kHz to about 40 kHz.

A pulse of air is applied to air cylinders in the actuator which actuates the ultrasonic horn against the anvil at a level effective to couple the ultrasonic energy into the product. This pulse can be represented as a static force that is applied to the ultrasonic horn to cause it to expand and contract, generating ultrasonic energy to destroy microorganisms on a product. Preferably, the pulse is generated by air at a pressure of from about 0.01 MPa to about 0.5 MPa. More preferably, the pulse is generated by air at a pressure of from about 0.01 MPa to about 0.14 MPa; still more preferably about 0.07 MPa.

The ultrasonic energy generated by the ultrasonic horn assembly is at a frequency of an effective amount to destroy the microorganisms present on the product. Specifically, the exertion of the ultrasonic energy on the product results in a microorganism destruction rate of at least about a 1-log kill. More preferably, the microorganism destruction rate is at least about a 2-log kill. Still more preferably, the microorganism destruction rate is at least about a 2.5-log kill.

For purposes of the present invention, it is contemplated that the term "product" includes the outer package of an item, as well as an item contained within an outer packaging, as microorganisms may be present on or within one or the other or both. For example, microorganisms may be present on the box or wrapper of an item. By way of further example, microorganisms may be present on an item contained within a box or wrapper. It is also contemplated that the term "product" includes letters, packages, or other articles of mail.

Representative microorganisms that may be destroyed by the process of the present invention include pathogenic bacteria, viruses, mycoplasma, fungi, parasites, and their reproductive elements (e.g., spores). Representative pathogenic bacteria that may be destroyed by the process of the present invention include *Salmonella* spp., *Clostridium botulinum, Staphylococcus aureus, Campylobacter jejuni, Yersinia enterocolitica* and *Yersinia pseudotuberculosis, Listeria monocytogenes, Vibrio cholerae* O1, *Vibrio cholerae* non-O1, *Vibrio parahaemolyticus* and other *Vibrios* spp., *Vibrio vulnificus, Clostridium perfringens, Bacillus cereus, Aeromonas hydrophila* and other spp., *Plesiomonas shigelloides, Shigella* spp., *Miscellaneous enterics* (including *Klebsiella, Enterobacter, Proteus, Citrobacter, Aerobacter, Providencia, Serratia*), *Escherichia coli*, and *Streptococcus* spp. Other representative microorganisms that may be destroyed by the process of the present invention include filamentous fungi such as, for example, *Aspergillus, Penicillium, Fusarium*, and *Aureobasidium*; yeasts such as, for example, *Candida* and *Rhodotorula*; and pathogenic alga such as, for example, *Prototheca*. Specifically, it is also contemplated that *Bacillus anthracis* may be destroyed by the process of the present invention.

In order to achieve a microorganism destruction rate of at least about a 1-log kill, the product is subjected to ultrasonic energy from a single pulse generated by the ultrasonic horn assembly for not more than about 5 seconds. More preferably, the desired microorganism destruction rate may be achieved by subjecting the product to ultrasonic energy from a single pulse generated by the ultrasonic horn assembly for not more than about 4 seconds. Advantageously, these relatively short periods of ultrasonic pulse times allow the process of the present invention to be used in rapid process and manufacturing streams. Moreover, the process of the present invention will result in a microorganism destruction rate of at least about a 1-log kill, without harming the aesthetic and functional properties of the product.

In an alternative embodiment of the present invention, the product is subjected to ultrasonic energy from multiple pulses for shorter durations from an ultrasonic horn assembly. In another alternative embodiment of the present invention, the product is subjected to ultrasonic energy from multiple pulses for shorter durations from a plurality of ultrasonic horn assemblies. By way of example, it is contemplated that the product could rest on a moving conveyor belt or the like equipped with one or a plurality of ultrasonic horn assemblies and pass through the space in between the energy transfer surface of each ultrasonic horn and the outer peripheral surface of each anvil, receiving ultrasonic energy from each ultrasonic horn assembly as it moves down the line. By way of an alternative example, it is also contemplated that a moving conveyor belt could be partially or completely wrapped around one or a plurality of ultrasonic horns, with the moving conveyor belt itself acting as an anvil. By way of another example, it is contemplated that the product could be moved through a slot or the like equipped with one or a plurality of ultrasonic horn assemblies and pass through the space in between the energy transfer surface of each ultrasonic horn and the outer peripheral surface of each anvil, receiving ultrasonic energy from each ultrasonic horn assembly. Where two to five pulses are used, the pulse time is preferably about 0.5 seconds to about 1.0 seconds, the amplitude is preferably from about 0.004 centimeters to about 0.006 centimeters, and the pulse is preferably generated by air at a pressure of from about 0.1 MPa to about 0.14 MPa. Where six to ten pulses are used, the pulse time is preferably about 0.5 seconds to about 0.55 seconds, the amplitude is preferably from about 0.004 centimeters to about 0.006 centimeters, and the pulse is preferably generated by air at a pressure of from about 0.01 MPa to about 0.14 MPa.

The process of the present invention for decontaminating products, such as pieces of mail, for example, applies ultrasonic energy from the acoustic source directly to the product being decontaminated via a longitudinal plane wave. With this direct application process, significant losses in energy application to the product due to acoustic impedance changes associated with changing transmission mediums are avoided. The process of the present invention transmits energy directly into a product such that the energy does not have to pass through a gas or air where it can become less effective. With this setup, faster speeds are achieved and the process described herein can be used directly in-line in manufacturing processes.

Having described the invention in detail, it will be apparent that modifications and variations are possible without departing the scope of the invention defined in the appended claims. Furthermore, it should be appreciated that all examples in the present disclosure are provided as non-limiting examples.

EXAMPLE 1

In this Example, a Sample Product is infected with microorganisms. The Sample Product is subjected to the processes of the present invention and the rate of microbial destruction is measured. The aesthetic and functional properties of the Sample Product are also evaluated after being subjected to the processes of the present invention.

The ultrasonic horn assembly used in this Example was a Branson model 931AES Press System fitted with a 3"×2" 20 kHz, titanium block horn and a 2.5:1 gain booster (Branson Ultrasonics Corp., Danbury, Conn.). The Press System was fitted with a self-leveling plate, specifically, a model SN112 Auto Mechanical Squaring Base (Toman Tool Corp., Viroqua, Wis.). The Press System was powered by a Branson model 930MA 3000 Watt, 20 kHz Power Supply and controlled with a Branson model WPC-1 Weld Profile Controller (Branson Ultrasonics Corp., Danbury, Conn.).

The Sample Product was a 6.5 cm×5 cm sealed plastic flexible film pouch containing a 7 cm×2 cm, 44 oz./sq. yd. biocomponent spunbound film laminate (SFS) ultrasonically seamed to a 2.4 oz./sq. yd. neck-bonded laminate (NBL). The NBL was a three-layer, cross-directional stretchable elastic laminate consisting of an extruded case film (target weight 1.0 oz./sq. yd.) laminated between two layers of neck-stretched polypropylene spunbond facings. The Sample Product was constructed in this manner to evaluate the efficacy of the decontamination process with regards to both the microorganism kill rate and harm to the product itself.

The microorganisms were prepared for injection into the Sample Product by transferring one loopful of *Escherichia coli* (ATCC #8739, American Type Culture Collection, Manassas, Va.) and *Staphylococcus aureus* (ATCC #6538, American Type Culture Collection, Manassas, Va.) into a fresh 5 ml vial of Tripticase Soy Broth (TSB, BBL prepared culture media, Becton, Dickinson and Co., Sparks, Md.). The vials were then incubated overnight at 37° C. in an incubator/shaker (Innova 4000, New Brunswick Scientific, New Brunswick, N.J.). Following incubation, 1 ml samples of each microbial suspension was centrifuged using a microcentrifuge (Eppendorf Centrifuge 5417R, Brinkmann Instruments, Inc., Westbury, N.Y.). The supernatant was decanted from the resulting pellet and discarded, and a sterile swab was used to remove excess broth without disturbing the pellet. Sterile water (1 ml) was added to the vial to resuspend the pellet, and the vial was vortexed (Model K-550-G, Scientific Industries, Inc., Bohemia, N.Y.). A portion (0.5 ml) of this suspension was then added to 40 ml of sterile water and vortexed to produce the final bacterial suspension.

Each Sample Product was injected with 100 μl of the final bacterial suspensions of *Escherichia coli* and *Staphylococcus aureus* using a sterile syringe (#2-1498 Hamilton 810RN syringe, Supelco, Bellefonte, Pa.). After the bacterial sample was injected, the hole was sealed with packing tape (Scotch Brand 371) over the entire face of the Sample Product. Negative contamination controls were injected with 100 μl of sterile water. All prepared, injected samples were placed in coolers with ice packs to preserve the bacterial counts.

To treat the Sample Products with ultrasonic energy, the outline of the ultrasonic horn was traced onto the self-leveling plate with a pencil in order to determine where to place the Sample Product. Once the desired time, amplitude, and pressure were set, the Sample Product was placed face up in the center of the penciled outline. The Sample Product was then contacted with the ultrasonic horn generating ultrasonic energy at the desired settings. Following ultrasonication, all Sample Products were processed to determine the number of bacteria remaining. Additionally, the aesthetic and functional qualities of the Sample Products were evaluated and rated. A rating of "Good" meant that no product destruction was observed and extremely little, if any, sticking of the non-woven portion to the packaging was observed. A rating of "Marginal" meant that the product stuck lightly to the packaging, with no melting of the non-woven portion observed. A rating of "Bad" meant that the product stuck tightly to the package, and that the non-woven portion melted.

To determine the rate of microbial destruction, each Sample Product was placed in 90 ml of 0.1% peptone water (VWR #25384-148, West Chester, Pa.) in a sterile cup. The cup was placed on a shaker for 10 minutes at 90-110 rpm. Then, 1 ml of liquid from the cup was placed into a tube containing 9 ml of 0.9% saline, and vortexed for 3 to 5 seconds. From the cup, 1 ml aliquots were placed into Petri plates in duplicate. From the vortexed tube, 1 ml aliquots and 0.1 ml aliquots were placed in Petri plates in duplicate. Into each plate was then poured 15 ml TSA media (PML#P2600, PML Microbiologicals, Wilsonville, Oreg.) at 45° C.+/−2° C. The plates were incubated at 35° C.+/−2° C. for 48 hours.

Following incubation, the plates were enumerated by visually counting the colonies present on the plates. An average of the dilution of the duplicate "countable" (30-300 CFU/plate) plates was taken and that number was multiplied by the appropriate factor. Where plates had >300 CFU/plate at the highest dilution, they were designated "TNTC" (too numerous to count). Where no growth occurred, plates were recorded as <90 CFU/plate. Log kill was then defined as the log of the average CFU recovered from the untreated bacteria-injected Product Samples minus the log of the average CFU recovered from the treated bacteria-injected Product Samples. Results are shown in Table 1 below.

TABLE 1

EFFECT OF ULTRASONIC TREATMENT ON LOG-KILL AND PRODUCT QUALITY

| | Ultrasonic System Set Points | | | Effect on Product | |
|---|---|---|---|---|---|
| Test Organism | Treatment Time (sec) | Energy Amplitude (%) | Pressure of Horn on Product (PSIG) | Log Kill | Product Quality |
| E. coli | 5 | 10 | 70 | 0.0 | Good |
| E. coli | 5 | 20 | 60 | 0.3 | Marginal |
| None | 5 | 30 | 50 | N/A | Bad |
| E. coli | 4 | 10 | 80 | 0.0 | Good |
| E. coli | 4 | 20 | 80 | 0.0 | Marginal |
| E. coli | 4 | 80 | 20 | 1.2 | Good |
| None | 4 | 80 | 40 | N/A | Bad |
| E. coli | 4 | 83 | 10 | 2.3 | Good |
| E. coli | 4 | 88 | 10 | 2.4 | Marginal |
| E. coli | 4 | 100 | 10 | 3.0 | Marginal |
| None | 4 | 100 | 20 | N/A | Bad |
| E. coli | 4 × 1 sec pulse | 90 | 10 | 1.2 | Marginal |
| E. coli | 8 × 0.5 sec pulse | 100 | 10 | 1.1 | Good |

TABLE 1-continued

EFFECT OF ULTRASONIC TREATMENT ON LOG-KILL AND PRODUCT QUALITY

| | Ultrasonic System Set Points | | | Effect on Product | |
|---|---|---|---|---|---|
| | Treatment | Energy | Pressure of | | |
| Test Organism | Time (sec) | Amplitude (%) | Horn on Product (PSIG) | Log Kill | Product Quality |
| E. coli | 6 × 0.5 sec pulse | 100 | 10 | 2.5 | Good |
| E. coli | 6 × 0.55 sec pulse | 100 | 10 | 1.2 | Good |
| E. coli | 6 × 0.55 sec pulse | 100 | 10 | 1.7 | Good |
| S. aureus | 6 × 0.55 sec pulse | 100 | 10 | 2.6 | Good |

What is claimed is:

1. A process for minimizing microorganisms on or in a product using ultrasonic energy, the process comprising:
contacting the product with an ultrasonic horn assembly comprising an ultrasonic horn and an anvil, and
generating a single pulse from the ultrasonic horn assembly for not more than about five seconds to excite the ultrasonic horn to an amplitude which generates ultrasonic energy at a frequency of an effective amount to destroy the microorganisms, wherein the ultrasonic energy results in a microorganism destruction rate of at least about a 1-log kill.

2. The process as set forth in claim 1 wherein the pulse lasts for not more than about 4 seconds.

3. The process as set forth in claim 1 wherein the pulse lasts for not more than about 3 seconds.

4. The process as set forth in claim 1 wherein the pulse lasts for not more than about 2 seconds.

5. The process as set forth in claim 1 wherein the pulse lasts for not more than about 1 second.

6. The process as set forth in claim 1 wherein the amplitude of the ultrasonic horn is less than about 0.013 centimeters.

7. The process as set forth in claim 1 wherein the amplitude of the ultrasonic horn is from about 0.0006 centimeters to about 0.006 centimeters.

8. The process as set forth in claim 1 wherein the amplitude of the ultrasonic horn is from about 0.004 centimeters to about 0.006 centimeters.

9. The process as set forth in claim 1 wherein the frequency of the ultrasonic energy is less than about 50 kHz.

10. The process as set forth in claim 1 wherein the frequency of the ultrasonic energy is from about 20 kHz to about 40 kHz.

11. The process as set forth in claim 1 wherein the pulse is generated by air at a pressure of from about 0.01 MPa to about 0.5 MPa.

12. The process as set forth in claim 1 wherein the pulse is generated by air at a pressure of from about 0.01 MPa to about 0.14 MPa.

13. The process as set forth in claim 1 wherein the pulse is generated by air at a pressure of about 0.07 MPa.

14. The process as set forth in claim 1 wherein the ultrasonic horn is a rotary ultrasonic horn and wherein the anvil is a rotary anvil.

15. The process as set forth in claim 1 wherein the product is a piece of mail.

16. A process for minimizing microorganisms on or in a product using ultrasonic energy, the process comprising:
contacting the product with at least one ultrasonic horn assembly comprising an ultrasonic horn and an anvil, and
generating two to five pulses from the ultrasonic horn assembly for not more than about 1 second to excite the ultrasonic horn to an amplitude which generates ultrasonic energy at a frequency of an effective amount to destroy the microorganisms, wherein the ultrasonic energy results in a microorganism destruction rate of at least about a 1-log kill.

17. The process as set forth in claim 16 wherein each pulse lasts for about 0.5 seconds to about 1 second.

18. The process as set forth in claim 16 wherein the amplitude of the ultrasonic horn is less than about 0.013 centimeters.

19. The process as set forth in claim 16 wherein the amplitude of the ultrasonic horn is from about 0.004 centimeters to about 0.006 centimeters.

20. The process as set forth in claim 16 wherein the frequency of the ultrasonic energy is less than about 50 kHz.

21. The process as set forth in claim 16 wherein the frequency of the ultrasonic energy is from about 20 kHz to about 40 kHz.

22. The process as set forth in claim 16 wherein the pulse is generated by air at a pressure of from about 0.01 MPa to about 0.14 MPa.

23. The process as set forth in claim 16 wherein the pulse is generated by air at a pressure of about 0.07 MPa.

24. The process as set forth in claim 16 wherein the ultrasonic horn is a rotary ultrasonic horn and wherein the anvil is a rotary anvil.

25. The process as set forth in claim 16 wherein the product is a piece of mail.

26. A process for minimizing microorganisms on or in a product using ultrasonic energy, the process comprising:
contacting the product with at least one ultrasonic horn assembly comprising an ultrasonic horn and an anvil, and generating six to ten pulses from the ultrasonic horn assembly for not more than about 0.55 seconds to excite the ultrasonic horn to an amplitude which generates ultrasonic energy at a frequency of an effective amount to destroy the microorganisms, wherein the ultrasonic energy results in a microorganism destruction rate of at least about a 1-log kill.

27. The process as set forth in claim 26 wherein each pulse lasts for about 0.5 seconds to about 0.55 seconds.

28. The process as set forth in claim 26 wherein the amplitude of the ultrasonic horn is less than about 0.013 centimeters.

29. The process as set forth in claim 26 wherein the amplitude of the ultrasonic horn is from about 0.004 centimeters to about 0.006 centimeters.

30. The process as set forth in claim 26 wherein the frequency of the ultrasonic energy is less than about 50 kHz.

31. The process as set forth in claim 26 wherein the frequency of the ultrasonic energy is from about 20 kHz to about 40 kHz.

32. The process as set forth in claim 26 wherein the pulse is generated by air at a pressure of from about 0.01 MPa to about 0.14 MPa.

33. The process as set forth in claim 26 wherein the pulse is generated by air at a pressure of about 0.07 MPa.

34. The process as set forth in claim 26 wherein the ultrasonic horn is a rotary ultrasonic horn and wherein the anvil is a rotary anvil.

35. The process as set forth in claim 26 wherein the product is a piece of mail.

* * * * *